United States Patent [19]

Horowitz

[11] Patent Number: 4,983,183
[45] Date of Patent: Jan. 8, 1991

[54] HIP PROSTHESIS AND METHOD FOR IMPLANTING THE SAME

[76] Inventor: Stephen M. Horowitz, 1233 York Ave., Apt. 7L, New York, N.Y. 10021

[21] Appl. No.: 410,666

[22] Filed: Sep. 21, 1989

Related U.S. Application Data

[62] Division of Ser. No. 306,946, Feb. 6, 1989.

[51] Int. Cl.⁵ .......................... A61F 2/32; A61F 2/30
[52] U.S. Cl. ........................................ 623/23; 623/16
[58] Field of Search ............... 606/92, 93, 94; 623/66, 623/16, 18, 22, 23

[56] References Cited

U.S. PATENT DOCUMENTS

| | | | |
|---|---|---|---|
| 3,112,743 | 12/1963 | Cochran et al. | 606/93 |
| 4,274,163 | 6/1981 | Malcom et al. | 606/94 |
| 4,462,394 | 7/1984 | Jacobs | 606/93 |
| 4,711,233 | 12/1987 | Brown | 606/94 |

Primary Examiner—David J. Isabella
Attorney, Agent, or Firm—Richard B. Klar

[57] ABSTRACT

The present invention relates to a hip prosthesis and a method of implanting the same utilizing dual modes of fixation. The prosthesis has a proximal portion which is porous coated to permit bone ingrowth. The prosthesis also has a distal stem portion which is adapted to be affixed by cementation. In addition, there is a tapering at the junction between the distal stem portion and the proximal portion. The prosthesis is implanted by reaming and broaching the femoral stem of a patient so that it can have a prosthesis' porous portion in contact with the bone proximally and still have channels between the bone and the distal stem portion which are cement filled. In addition this design also allows an improvement in cementation technique by providing an improved bone-cement interlock by more efficient pressurization.

8 Claims, 3 Drawing Sheets

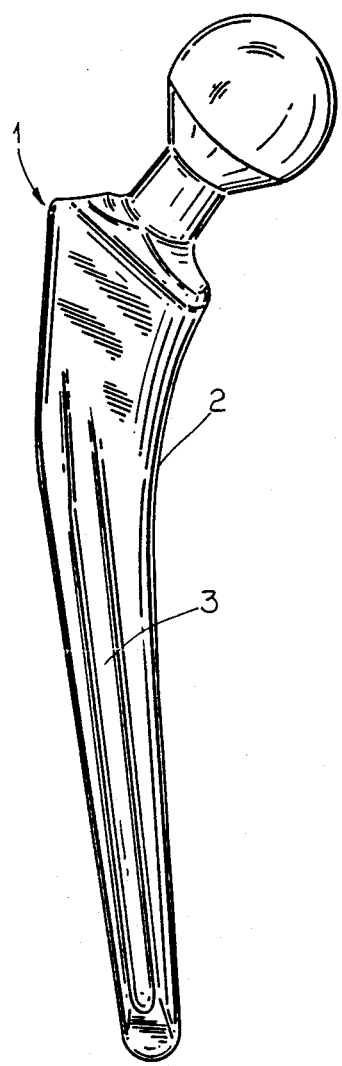
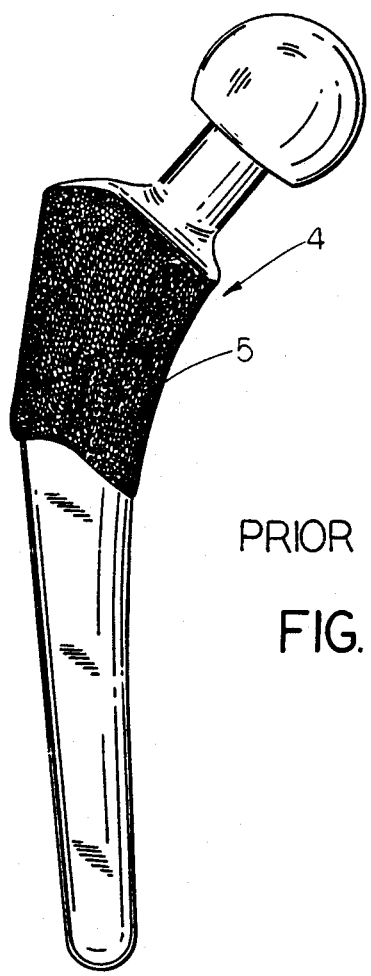
PRIOR ART
FIG. 2
PRIOR ART
FIG. 1

HIP PROSTHESIS AND METHOD FOR IMPLANTING THE SAME

This is a divisional of co-pending application Ser. No. 07/306,946 filed on Feb. 6, 1989.

BACKGROUND OF THE INVENTION

The present invention relates to a hip prosthesis and a method for implanting the same in a patient. In particular, the present invention relates to a prosthesis and method of implanting the same which depends upon two types of fixation.

Hip prosthesis are known in the art. One of the most common types of fixation techniques used for hip prosthesis is fixation by cementation by typically using polymethlymethacrylate cement. Using a surgical device called a broach, a canal is constructed in the femoral shaft of a patient which will accommodate the femoral stem of the prosthesis. However, before inserting the prosthesis but after broaching the canal, cement is poured into the canal and the stem of the prosthesis is fully inserted therein so that the entire length of the femoral stem of the prosthesis is affixed by cementation.

One of the problems associated with cement fixation of hip prosthesis is eventual failure due to aseptic loosening of the prosthesis in the patient. It has been shown that this occurs in as many as 15-20 percent of cemented hip replacements as early as 10-15 years following implantation. It has been shown that the reason for such failure is probably due to certain movement known as micromotion at the bone-cement interface which leads to the generation of polymethylmethacrylate particles which result in a foreign loosening and the eventual failure of the cemented hip prosthesis. This activity has been the subject of research and such research has been documented in an article entitled "Effects of Polymethylmethacrylate Exposure Upon Macrophages" published in the *Journal of Orthopaedic Research* Vol. 6, No. 6, 1988, and of which the applicant is a co-author.

In addition, other researchers have shown that improvements in cement techniques such as cementation under pressure leads to improved bone cement interlock resulting in increased longevity for the cemented prostheses.

Another and more recent technique of fixation for a hip prosthesis is through the use of a porous ingrowth surface. With this technique, the prosthesis is porous coated to allow bone ingrowth. This technique was developed in an attempt to construct a prosthesis which would last longer than the cemented designs.

At the present time, it is too soon to tell whether a porous ingrowth prosthesis will last longer than the cemented prosthesis. However, it has been shown that poor bone stock or any factor which impairs initial prosthesis fixation will lead to early micromotion at the porous/bone interface. This motion results in fibrous tissue ingrowth, rather than bone ingrowth. This lack of bone ingrowth has been implicated as a likely mode of failure of this prosthesis. Bone ingrowth into porous coated prosthesis occurs maximally during the critical period of the first six weeks of implantation. Accordingly, it would be advantageous to eliminate early micromotion so that a situation would exist allowing the maximum amount of bone ingrowth and resulting in the maximum longevity possible for the porous design. It would also be advantageous to use an additional mode of fixation in association with the porous design, then the design could be used in situations with poor bone stock.

SUMMARY OF THE INVENTION

Hence with the foregoing in mind, it is a principal object of the present invention to provide a prosthesis and a method of implanting the same which utilizes two types of fixation and thus avoids the drawbacks associated with the aforementioned prior art proposals.

It is a further object of the invention to provide a longer lasting prosthesis, particularly for younger patients expected to outlive one or more prostheses.

It is still another object of the invention to provide a prosthesis for patients with poor bone stock such as: 1. patients on medication which weaken bone such as steroids (which is used for arthritic patients who are frequent candidates for replacements) and 2. patients who have had prior prostheses removed (revision situations).

The present invention provides a prosthesis having a proximal, or calcar portion which is porous coated to allow bone ingrowth and a distal stem portion which relies on polymethylmethacrylate cement for fixation.

As noted previously, bone ingrowth into porous coated prosthesis occurs maximally during the first six weeks of implementation. The present invention utilizes cement for fixation of the stem of the prosthesis thus providing a superb early stabilization and ensuring the highest quality of bone ingrowth.

The reason this stability is often difficult to obtain with most current uncemented designs is that they do not use any method other than the interference fit of the stem in bone to achieve early prosthesis stability. This interference type fixation is particularly poor when the prosthesis is to be used for a revision, or any individual with poor quality bone such as patients receiving steroids. Such a situation can occur with candidates who are arthritic patients and must take steroid medication which results in poor bone stock. In fact, these two situations are considered by many to be cotraindications to the use of uncemented designs.

Cemented prostheses achieve maximal fixation soon after implantation. Particle generation secondary to micromotion does not really begin to become prominent until several years after prosthesis implantation.

Thus, the proposal of the present invention is that the use of cement will inhibit early micromotion and lead to a very high degree of bone ingrowth into the porous aspect of the prosthesis. In addition, it is proposed that this ingrowth will result in excellent fixation which will dramatically decrease later occurring motion at the bone-cement interface. This should impede the generation of particles and improve longevity. This improved prosthesis longevity would be particularly advantageous in younger patients, who are likely to outlive the life span of currently available prostheses.

The prosthesis and insertion technique of the present invention provides for a better bone-cement interlock which is due to drilling a hole at the lateral aspect of the hip around the level of the lesser trochanter to drain excess cement therethrough and due to the wedge effect of the proximal portion of the prosthesis wedging into the bone. The hole and the wedge effect of the proximal portion of the prosthesis results in better pressurization of the cement into the bone and improves the interlocking between the bone and the cement.

The present invention not only provides a prosthesis in which cement is used in a porous design but also offers a new design and altered cement technique which allows both bone ingrowth and cement fixation to occur simultaneously.

BRIEF DESCRIPTION OF THE DRAWINGS

For a fuller understanding of the nature and the objects of the invention, reference should be had to the following detailed description, taken in connection with the accompanying drawings, in which:

FIG. 1 is a perspective view of a prior art prosthesis;

FIG. 2 is a perspective view of another prior art prosthesis;

DETAILED DESCRIPTION OF THE PREFERRED EMBODIMENT

Figures 3, 4:
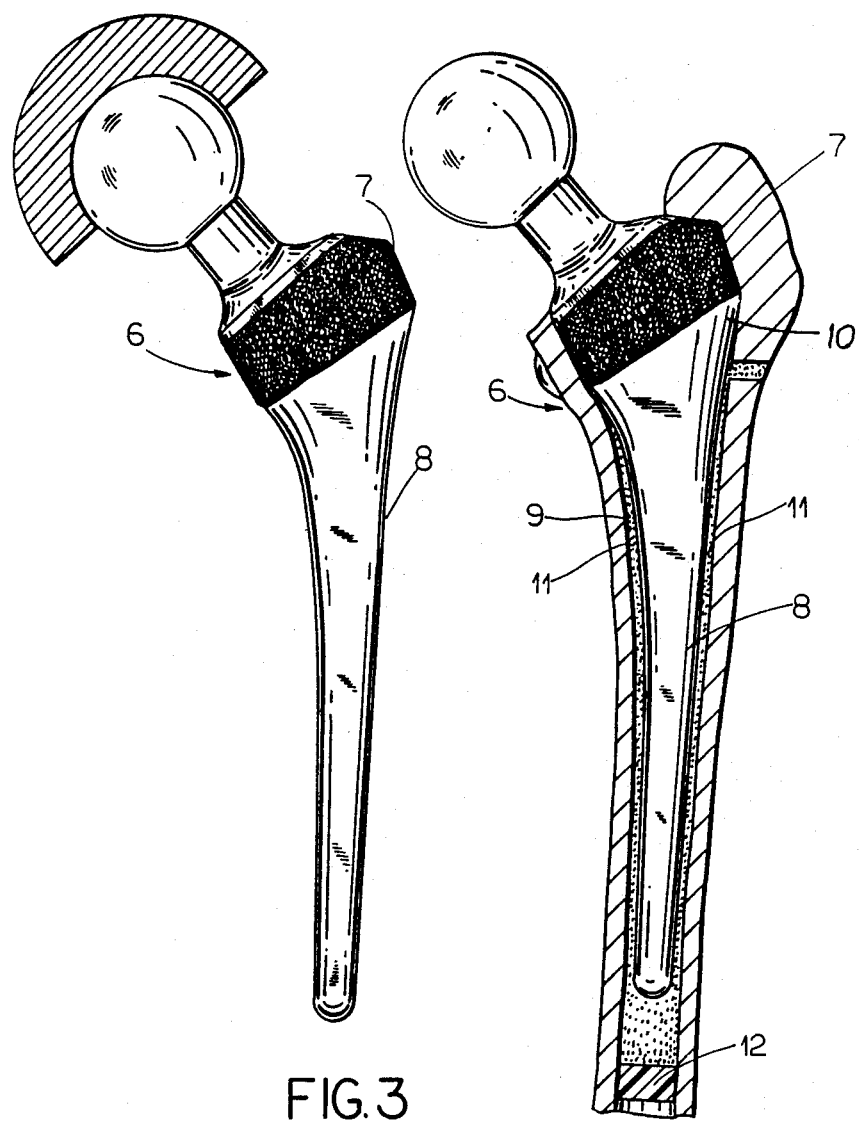
FIG. 3 is a perspective view of the prosthesis of the present invention.
FIG. 4 is a perspective view of the prosthesis of the present invention implanted within the femoral stem of a patient.

Referring now to the drawings, FIG. 1 discloses a prior art prosthesis 1 of the type which is affixed by cementation. The entire stem 2 of the prosthesis of FIG. 1 is cemented into the femoral stem of the patient. The stem 2 on such prosthesis may or may not have a longitudinal groove 3 to enhance cement fixation.

FIG. 2 disclose a prosthesis 4 having a porous contoured portion 5 to permit ingrown bone fixation when implanted in a patient.

FIG. 3 is the prosthesis 6 of the present invention. The prosthesis 6 has a proximal or calcar portion 7 which is porous coated for ingrown bone fixation. The prosthesis also has a distal stem portion 8 which is adapted to be cemented within the femoral stem 9 of the patient.

In FIG. 4 the prosthesis 6 is shown implanted within the patient. The proximal portion 7 of the prosthesis 6 which has the porous coating is preferably 15-20% of the length of the stem of the prosthesis as compared to 25-100% of the stem for a conventional uncemented, porous prosthesis. The 15-20% porous length provides a sufficient stem length for cementation. Further, it is preferable if the prosthesis is manufactured at longer lengths of currently available designs or approximately 10 cm longer than this in length.

The prosthesis is tapered at the junction 10 of the proximal portion and the distal portion as shown in FIGS. 3 and 4. This differs from the typical porous prosthesis in which the stem wedges into the bone of the patient. The distal stem of prosthesis does not wedge into the bone, as it is desired to have channels 11 which are filled with cement between the distal stem portion 8 of the prosthesis and the patient's bone 9. Thus, the prosthesis has a tapering at the junction 10 to permit 2 mm channels 11 throughout the length of the distal stem 8 of the prosthesis 6.

It is understood that the present invention is not limited to the aforementioned dimensions and any other as minimal modifications that would be obvious to one skilled in the art. One such example of a minor modification would be the addition of a proximal collar.

A cement retainer or plug 12 is placed below the prosthesis to prevent cement from flowing down within the patient as shown in FIG. 4 and FIGS. 5A-C. This also allows enhanced pressurization of the cement.

The porous coating for the prosthesis is preferably made of cobalt-chrome or a vitallium alloy or titanium. The stem is preferably formed of either cobalt-chrome or a titanium alloy although it is understood that any other such suitable materials can be used and the invention is not limited to these specific materials.

EXAMPLE

The preferred dimensions of the prosthesis include a porous coating of 1-2 cm. and a taper beginning with 0.5 cm of the end of the porous coating.

In utilizing a 9 mm uncemented prosthesis, the proximal dimension would stay the same, the porous coating would be reduced 1-2 cm, the distal stem diameter would be 8 mm (as compared to 9 mm for a conventional prosthesis) and the length of the prosthesis would be equal to the longer uncemented types (from 15-20 cm). As to the degree of tapering of the stem, the distal stem portion would be one mm length in diameter narrower than it would be in a conventional uncemented prosthesis.

It is understood that the above dimensions are given as one example and the invention is not limited to these dimensions.

Figures 5A, 5B, 5C:
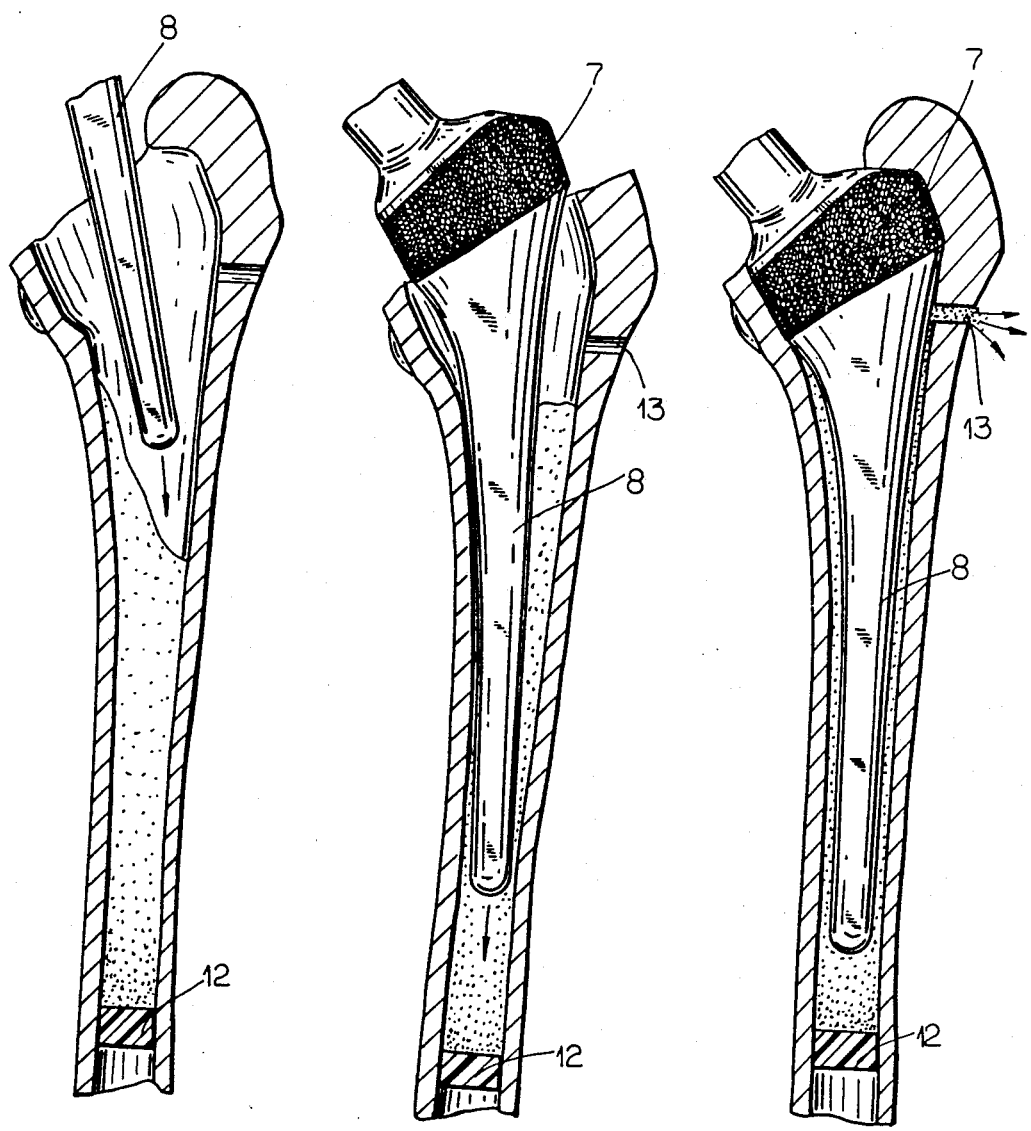
FIGS. 5A, 5B and 5C illustrate the method of implanting the prosthesis of FIG. 3 in accordance with the technique of the present invention.

FIGS. 5A-C illustrate the method of implanting the prosthesis in a patient.

Using a reamer and a broach, conventional surgical tools, the inner part of the bone is reamed and broached to the appropriate dimensions to accommodate the contours including the tapering of the prosthesis 6.

Preferably a converted 9 mm broach would be used. Also instead of reaming to a diameter of 9 mm distally, it is preferable to over ream to 10 mm to ensure continuous 2 mm channels between the prosthesis and the bone for the cement to filled therein.

A hole 13 is then drilled approximately ¼" in diameter at the lateral aspect of the hip around the level of the lesser trochanter as shown in FIGS. 5A-C. The hole 13 serves to permit any excess cement to be drained as therethrough.

After drilling the bone, a cement retainer or plug 12 as shown in FIGS. 5A-C is placed therein to prevent cement from flowing downward.

Cement is then injected through the neck of the femur. The level of the cement should be below the level of the hole 13 and preferably at a level of 2-3 cm. If too much cement is injected the excess amount will drain out of the hole 13. If too little cement is injected and the prosthesis is already inserted then more cement can be injected through the hole 13.

After the cement is injected, the prosthesis 6 is inserted through the neck of the femur. The proximal portion 7 of the prosthesis 6 wedges into the bone 9 and thus functions as an upper plug pressurizing any excess cement into flowing out through the hole 13. This wedge effect is yet another advantage of the present invention. There is an improved interlocking between the bone and the cement because of better pressurization of the cement into the bone due to the hole 13 and the wedge effect of the proximal portion 7 of the prosthesis 6.

I do not limit myself to any particular details of construction set forth in this specification and illustrated in the accompanying drawings, as the same refers to and sets forth only certain embodiments of the invention, and it is observed that the same may be modified without departing from the spirit and scope of the invention.

Having thus described the invention, what I claim as new and desire to be secured by Letters Patent is as follows:

1. A method of implanting a dual mode fixation hip prosthesis in a patient, the improvement comprising:
    preparing the intramedullary canal of the femoral stem;
    making a through hole in the lateral aspect of a patient's hip around the level of the lesser trochanter;
    injecting cement into the intramedullary canal wherein said hole drains out any excess cement thus maintaining the cement level below the level of the hole and;
    inserting a hip prosthesis having a distal stem portion adapted to be affixed by the cement and a proximal portion having a porous coating wherein said proximal portion is positioned above said hole such that excess cement drains out of the hole thereby maintaining the cement level below the proximal portion and allowing bone ingrowth into the porous coating and achieving dual modes of fixation of the prosthesis.

2. A method according to claim 1 further comprising the step of broaching and overreaming the femoral stem of the patient to form a circumferential gap between said distal stem of said prosthesis and the bone of the patient, said channels being cement filled after the cement is injected therein.

3. A method according to claim 1 wherein insertion of the proximal portion creates a wedging effect against the patient's bone and said wedge-like effect and said hole provide a more efficient pressurization for the cement surrounding the lower stem portion for cement into bone interlocking.

4. A method according to claim 1 wherein said circumferential gap is approximately 2 mm in diameter.

5. A method according to claim 1 wherein the cement injected into the patient's femoral stem is polymethylmethacrylate cement.

6. A method according to claim 1 wherein said hole is made by drilling.

7. A method according to claim 6 wherein said hole is drilled to approximately ¼ inch in diameter.

8. A method according to claim 1 wherein prior to injecting the cement into the canal a cement retainer is inserted into the canal at a distance distal to a distal end of the prosthesis when the prosthesis is placed in the canal thereby preventing cement from flowing further downwardly into the canal.

* * * * *